United States Patent
Liu et al.

(10) Patent No.: US 11,993,813 B2
(45) Date of Patent: May 28, 2024

(54) NUCLEIC ACID PROBE AND NUCLEIC ACID SEQUENCING METHOD

(71) Applicant: MGI TECH CO., LTD., Shenzhen (CN)

(72) Inventors: Erkai Liu, Shenzhen (CN); Wenwei Zhang, Shenzhen (CN); Ao Chen, Shenzhen (CN); Chongjun Xu, Shenzhen (CN)

(73) Assignee: MGI TECH CO., LTD., Guangdong (CN)

( * ) Notice: Subject to any disclaimer, the term of this patent is extended or adjusted under 35 U.S.C. 154(b) by 1123 days.

(21) Appl. No.: 16/643,161

(22) PCT Filed: Jul. 6, 2018

(86) PCT No.: PCT/CN2018/094902
§ 371 (c)(1),
(2) Date: Feb. 28, 2020

(87) PCT Pub. No.: WO2019/042016
PCT Pub. Date: Mar. 7, 2019

(65) Prior Publication Data
US 2020/0277673 A1    Sep. 3, 2020

(30) Foreign Application Priority Data

Aug. 31, 2017 (CN) .......................... 201710766925.0

(51) Int. Cl.
| | | |
|---|---|---|
| C12Q 1/68 | (2018.01) | |
| C07H 21/00 | (2006.01) | |
| C12Q 1/6811 | (2018.01) | |
| C12Q 1/6853 | (2018.01) | |
| C12Q 1/6874 | (2018.01) | |
| C12Q 1/6855 | (2018.01) | |

(52) U.S. Cl.
CPC .......... *C12Q 1/6874* (2013.01); *C07H 21/00* (2013.01); *C12Q 1/68* (2013.01); *C12Q 1/6811* (2013.01); *C12Q 1/6853* (2013.01); *C12Q 1/6855* (2013.01)

(58) Field of Classification Search
CPC ...... C12Q 1/6874; C12Q 1/68; C12Q 1/6811; C12Q 1/6853; C12Q 1/6855; C07H 21/00
See application file for complete search history.

(56) References Cited

U.S. PATENT DOCUMENTS

| | | | |
|---|---|---|---|
| 11,649,489 B2* | 5/2023 | Liu ...................... | C12Q 1/6876 435/6.11 |
| 2003/0207295 A1 | 11/2003 | Gunderson et al. | |
| 2008/0003571 A1* | 1/2008 | McKernan .......... | C12Q 1/6874 435/6.12 |
| 2009/0170724 A1 | 7/2009 | Balasubramanian et al. | |
| 2011/0039259 A1 | 2/2011 | Ju et al. | |
| 2011/0076679 A1 | 3/2011 | Shin et al. | |

FOREIGN PATENT DOCUMENTS

| | | |
|---|---|---|
| CN | 1617937 A | 5/2005 |
| CN | 101633961 A | 1/2010 |
| CN | 101910410 A | 12/2010 |
| CN | 102030792 A | 4/2011 |
| CN | 103602719 A | 2/2014 |
| CN | 104520443 A | 4/2015 |
| CN | 105722850 A | 6/2016 |
| WO | WO 03/048387 A2 | 6/2003 |
| WO | WO 2009/055617 A1 | 4/2009 |
| WO | WO 2013/188471 A2 | 12/2013 |
| WO | WO 2015/026845 A2 | 2/2015 |

OTHER PUBLICATIONS

Ansorge, "Next-generation DNA sequencing techniques", New Biotechnology, 2009, 25(4): 195-203.
Ju et al., "Four-color DNA sequencing by synthesis using cleavable fluorescent nucleotide reversible terminators", PNAS, 2006, 103(52): 19635-19640.
Mardis, "The impact of next-generation sequencing technology on genetics", Trends in Genetics, 2008, 24(3): 133-141.
Liu et al., "Chlamydia pneumoniae AP endonuclease IV could cleave AP sites of double- and single-stranded DNA", Biochimica et Biophysica Acta, 2005, 1753: 217-225.
Seo et al., "Four-color DNA sequencing by synthesis on a chip using photocleavable fluorescent nucleotides", PNAS, 2005, 102(17): 5926-5931.
Wan et al., "Evaluation of a New HPV Genotyping Assay Based on Semiconductor Sequencing Method", China J. Fam Plann, 2015, 23(9): 615-619.
Jiang et al., "Cleavable Linkers in DNA Sequencing by Synthesis", Progress in Chemistry, 2016, 28(1): 58-66.

* cited by examiner

*Primary Examiner* — Jezia Riley
(74) *Attorney, Agent, or Firm* — James S. Keddie; Bozicevic, Field & Francis LLP

(57) ABSTRACT

A nucleic acid probe and a nucleic acid sequencing method for performing sequencing while ligating nucleic acids. The nucleic acid probe is a DNA sequencing probe, comprising a first moiety, a second moiety, a linker, and a detectable label. A base of the first moiety is A, T, U, C, or G, a base of the second moiety is a random base and/or a universal base, and 3 bases or more are present in the second moiety. The first moiety and the second moiety are ligated via the linker, the connection between the first moiety and the ligation can be cleaved, and the detectable label is ligated to the second moiety or the linker. The above probe, a combination formed therewith, or a sequencing method using the same can reduce the number or types of probes in nucleic acid sequencing, thereby reducing cost.

13 Claims, 1 Drawing Sheet

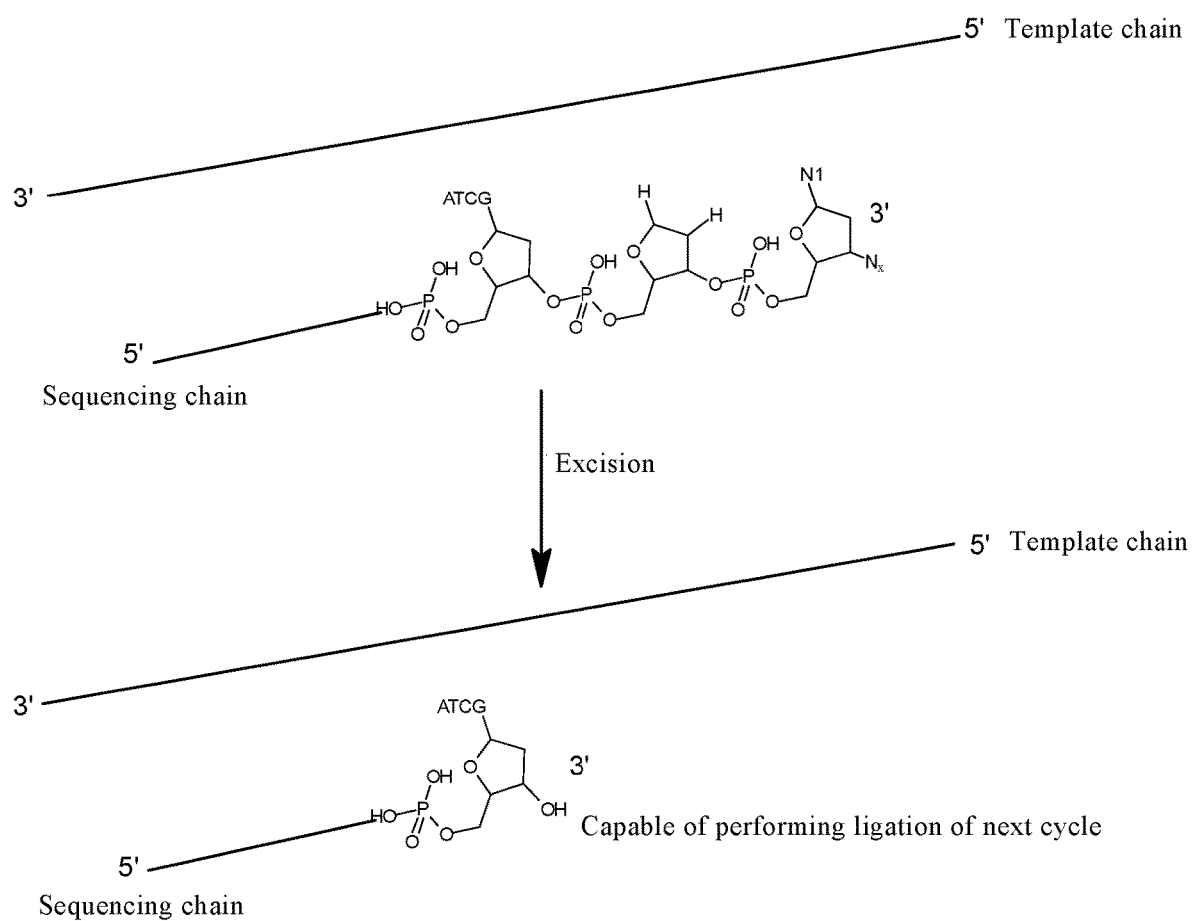

NUCLEIC ACID PROBE AND NUCLEIC ACID SEQUENCING METHOD

RELATED APPLICATIONS

This application is a U.S. National Phase application, filed under 35 U.S.C. § 371(c), of International Application No. PCT/CN2018/094902, filed Jul. 6, 2018, which claims priority to, and the benefit of, Chinese Patent Application No. 201710766925.0, filed Aug. 31, 2017, the entire contents of both of which are herein incorporated by reference.

TECHNICAL FIELD

The invention belongs to the field of gene sequencing and relates to a nucleic acid probe and a nucleic acid sequencing method. In particular, the nucleic acid probe is a DNA sequencing probe. In particular, the nucleic acid sequencing method is a nucleic acid sequencing method that performs sequencing while ligating.

BACKGROUND ART

The technology of sequencing-by-ligation was developed by Complete Genomics and ABI, respectively, and presented in different forms. The basic principle thereof is that a fluorescently modified DNA probe is ligated by a ligase. The DNA probe is a specific base at certain position to identify the sequence to be tested, and the remaining positions are random sequences to form a complementary strand with another position to be tested. After the ligation reaction, the probe that is not ligated is removed, and then the signal of the ligated probe is detected by an optical means to determine the sequence at that position.

Complete Genomics uses probes that mark four different bases with different fluorophores. There are 4 different bases at the first position of the 5'-terminal of the first group of probes, and the subsequent bases are a random sequence that can bind to a random sequence to be tested. After being ligated to a primer sequence by a ligase, a fluorescence is detected to obtain the base information at that position. After removing the added sequence and adding a new sequencing primer, the hybridization and ligation of the second group of probes are performed. There are 4 different bases at the second position of the 5'-terminal of the second group of probes, and there are random sequences at the other positions. After that, the fluorescent molecule at the second position is detected to determine the sequence at the second position. Similarly, the base sequences at positions 3 to 8 are determined, respectively. A total of 8 groups of probes are used to determine the sequence of the first eight bases, and then longer new sequencing primers are added to carry out the sequencing of the next eight bases.

The ligation sequencing method of ABI is called as Sequencing by Oligonucleotide Ligation and Detection (SOLiD), which uses 16 different groups of probes. The first two bases of each group of probes are a fixed sequence, the next three bases are a random sequence, and the following three bases are universal bases; the method for ligating random bases and universal bases (5th and 6th) is O—P—S, and the above sequences can be sorted from the 5'-terminal or the 3'-terminal. As shown in the following formula I, if sorted from the 5'-terminal, the 3'-terminal of the random base is an oxygen atom, and the 5'-terminal of the first universal base is a sulfur atom. Similarly, if sorted from the 3'-terminal, the 5'-terminal of the third random base is an oxygen atom, and the 3'-terminal of the first universal base is a sulfur atom.

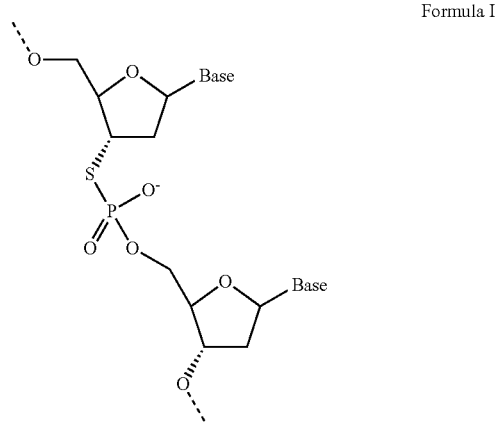

Formula I

The sequencing is performed from the 3' end to the 5' end: a sequencing primer is added, a sequencing probe is used for ligation and detection; in the ligation reaction system, the template and primers are complementarily paired, the primers are connected to magnetic beads and photographed directly. Silver ions are used for excision (silver ions can specifically be bound with sulfur elements to cleave S—P bond, and after the cleavage P is connected to hydroxide ions and S is connected to silver ions), so that all universal bases are excised, a phosphate group is remained at the 5'-terminal direction, and ligation is carried at the position after 5 bases in the next cycle. After multiple repeating, the sequencing strand is removed and a new primer is hybridized thereon, wherein the new primer has one more base than the previous one; after multiple repeating the cycle again, the sequencing strand is removed and the primer for the third time is hybridized thereon. In this way, after multiple repeating, the entire sequence can be ligated, and the sequence information of each position can be determined through the cross-comparison of the signals.

The method of sequencing by DNA ligation reaction has the following shortcomings: (1) due to the large number or many kinds of probes, the cost is relatively high; (2) since 5 bases should be added each time in the SOLiD method, the sequencing primers have to be loaded after one or several cycles, which increases the sequencing cost and time cost; (3) the excision method is not friendly to the sequencing system. As a biochemical reaction in the sequencing, many enzymes are very sensitive to transition metals. In addition, the used silver ions are prone to remain and will inevitably affect the subsequent experiments. For example, the reaction buffer may contain chloride ions, while silver ions can react with chloride ions to generate precipitation easily. In addition, silver ions may also react with T bases to form a mismatch of T-Ag-T structure.

Therefore, there is still a need to develop a new sequencing method, especially a new method of nucleic acid sequencing by ligation that is more efficient and lower cost.

Contents of the Invention

After intensive research and creative labor, the inventors skillfully designed a nucleic acid probe, and based on this, obtained a method for nucleic acid sequencing using the nucleic acid probe. The inventors have surprisingly found that the new sequencing method uses only four groups of probes, which significantly reduces the number of probes and can effectively reduce costs; the probes designed by the present invention will only add one base to the sequencing chain after each cycle; therefore, with the continuous extension of sequencing, there is no need to replace sequencing primers, which also reduces cost. In addition, in the present invention, a new kind of rapid excision method is used for the excision of the redundant part of the probe, which reduces the damage to the sequencing system and is beneficial to improve the reads of the sequencing. The following inventions are thus provided:

One aspect of the invention relates to a nucleic acid probe comprising a first moiety, a second moiety, a linker and a detectable label, wherein:
 the first moiety has a base of A, T, U, C or G,
 the second moiety has random bases and/or universal bases, and the number of the bases is 3 or more,
 the first moiety is ligated to the second moiety via the linker, and the ligation between the first moiety and the linker can be cleaved,
 the detectable label is ligated to the second moiety or the linker.

In the present invention, unless otherwise specified, the nucleic acid probe is also simply referred to as a probe.

In the present invention, the first moiety and the second moiety are only used for clarity and have no sequential meaning.

In the present invention, the first moiety is a sequencing base.

In one embodiment of the invention, the first moiety is located at the 5'-terminal or the 3'-terminal; preferably, the first moiety is located at the 5'-terminal. If the first base at the 3'-terminal of the probe is a sequencing base, the detectable label and/or the chemical group can be designed at the 5'-terminal; otherwise, if the first base at the 5'-terminal is a sequencing base, the detectable label and/or the chemical group can be at the 3'-terminal.

In one embodiment of the present invention, the bases of the second moiety are random bases.

In one embodiment of the present invention, the bases of the second moiety are universal bases.

In one embodiment of the present invention, the bases of the second moiety are both random bases and universal bases.

In some embodiments of the present invention, the bases of the second moiety are 3 to 15 bases, preferably 5 to 12 bases, and more preferably 5 to 10 bases (for example, 5, 6, 7, 8, 9, or 10 bases), particularly preferably 6 to 9 bases. Without being bound by any theory, the preferred probe has a length determined by taking into account the stability of hybridization between the probe and template and the cost for synthesis of the probe.

The end of the second moiety is blocked, which means that there is not a free 3'-OH at the end of the second moiety, so it cannot form a new 3',5'-phosphodiester bond, that is, it cannot be ligated to another probe.

In one embodiment of the present invention, when the ligation between the first moiety and the linker is cleaved, the 3'-terminal OH or 5'-terminal phosphate group of the first moiety is exposed.

In one embodiment of the invention, when the ligation between the first moiety and the linker is cleaved, the second moiety and the linker are removed.

In one embodiment of the present invention, preferably, the detectable label is ligated to the second moiety;

Preferably, the detectable label is ligated to 3'-OH at the end of the second moiety;

Preferably, the detectable label is ligated to 3'-OH at the end of the second moiety by a phosphoester bond.

In some embodiments of the present invention, wherein the detectable label is a fluorophore, preferably one or more selected from the group consisting of cy3, cy5, Texas Red, 6-FAMTM, AF532, AF647 and AF688; preferably, the fluorophore is ligated to 3'-OH at the end of the second moiety; preferably, the fluorophore is ligated to 3'-OH at the end of the second moiety via a phosphoester bond. The probe is now blocked. For example, the following Formula II or Formula III is shown:

Formula II

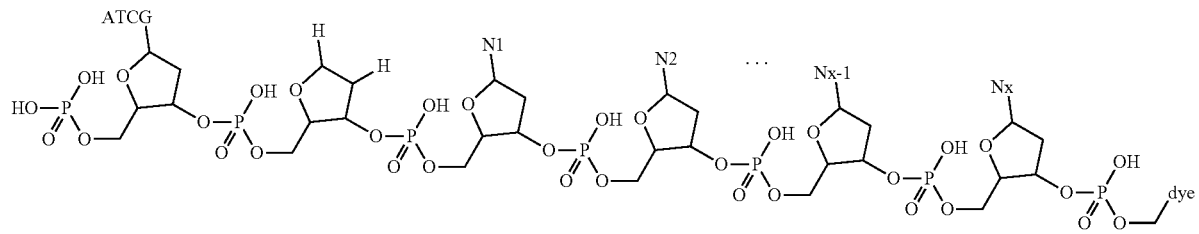

In Formula II, 5' is a sequencing base, and 3' is a fluorophore.

In the following Formula III, 3' is a sequencing base, and 5' is a fluorophore.

Formula III

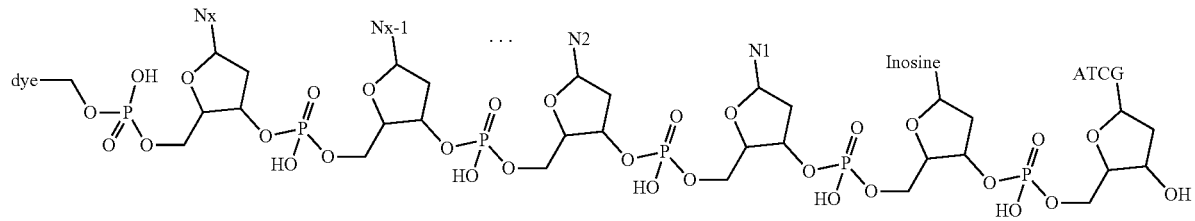

The ligation between the first moiety and the linker can be cleaved in different ways, so that the 3'-terminal OH or 5'-terminal phosphate group can be exposed for the next cycle of sequencing reactions. Preferably, the linker does not contain a sulfur atom; preferably, the linker is selected from the group represented by the following Formula IV to Formula IX:

Formula IV

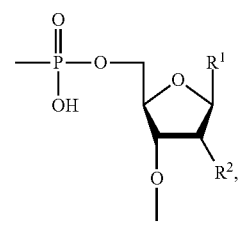

Formula V

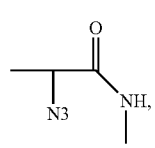

Formula VI

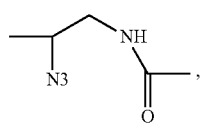

Formula VII

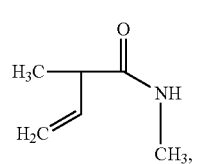

Formula VIII

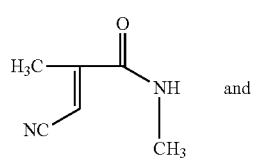

and

Formula IX

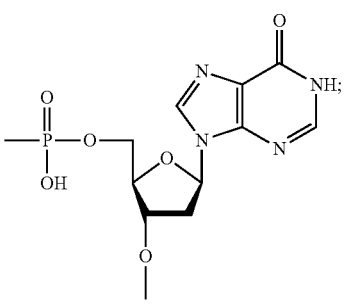

In Formula IV, $R^1$ is selected from a group consisting of H, OH, $C_1$-$C_6$ alkyl, $C_2$-$C_6$ alkenyl, and $C_2$-$C_6$ alkynyl; $R^2$ is selected from a group consisting of H, OH, F, Cl, and Br.

The ligation modes represented by the groups of the above Formula IV to Formula IX are abbreviated as AP site, azide, azide, allyl, cyanovinyl and inosine sites, respectively. The excision methods in sequence are Endonuclease IV, organic phosphide, organic phosphide, palladium catalyst, organic phosphide, and hAAG enzyme+endonuclease IV, respectively.

The methods for ligation and excision of the groups represented by the Formula IV to Formula IX can be methods known to those skilled in the art and may also refer to the following description.

(1) AP Site Ligation Mode

Formula X

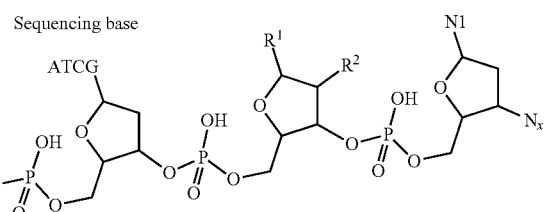

The sequencing base and the second base (N1) are ligated using a cyclic deoxyribose or deoxyribose derivative, and a specific ligation method may refer to Xipeng Liu, Jianhua Liu. The mechanism of base excision repair in *Chlamydiophila pneumoniae*. DNA Repair 4 (2005) 1295-1305. The above Formula X is a structural formula with 5'-terminal sequencing base, wherein $R^1$ is selected from H, OH, $C_1$-$C_6$ alkyl, $C_2$-$C_6$ alkenyl and $C_2$-$C_6$ alkynyl; $R^2$ is selected from H, OH, F, Cl and Br.

(2) Two-Azide Ligation Modes

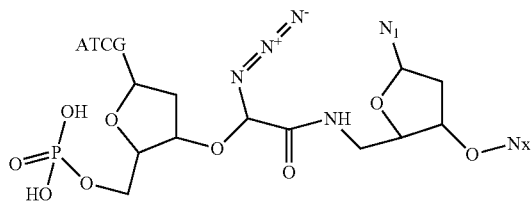

Formula XI

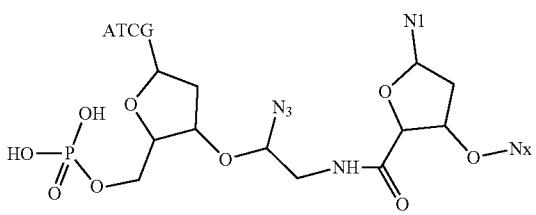

Formula XII

The method for ligation between the chemical group and the sequencing base in Formula XI or Formula XII may refer to the prior art, for example, U.S. Pat. No. 8,084,590 B2.

The ligation between the chemical group and the sequencing base in Formula XI or Formula XII may be cleaved by an organic phosphide (e.g., THPP, TCEP). The conditions for excision may be, for example, 100 mM TCEP, pH=7, 1 M sodium chloride, 5 minutes at 50° C.

(3) Allyl Ligation Mode

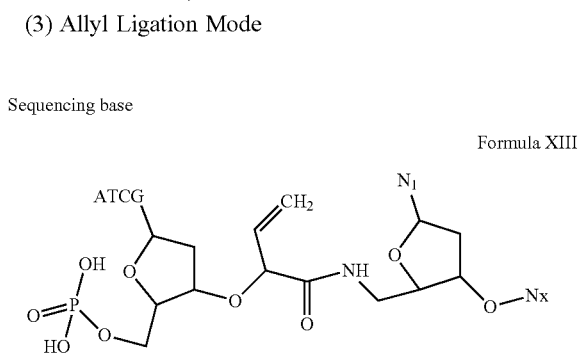

Formula XIII

The method for ligation between the chemical group and the sequencing base in Formula XIII may refer to the prior art, for example, Jingyue Ju, Dae Hyun Kim, et. al. Four-color DNA sequencing by synthesis using cleavable fluorescent nucleotide reversible terminators. PNAS. 2006. 103 19635-19640.

The ligation between the chemical group and the sequencing base in Formula XIII can be excised by a PdCl$_2$+ sulfonated triphenylphosphine complex. The operating conditions for the excision can be, for example, 20 mM Tris-HCl, 10 mM (NH$_4$)$_2$SO$_4$, 10 mM KCl, 2 mM MgSO$_4$, 0.1% Triton® X-100, pH 8.8, 1 mM Na$_2$PdCl$_4$, 5 mM P(PhSO$_3$Na)$_3$], reaction for 5 min at 60° C.

(4) Cyanovinyl Ligation Mode

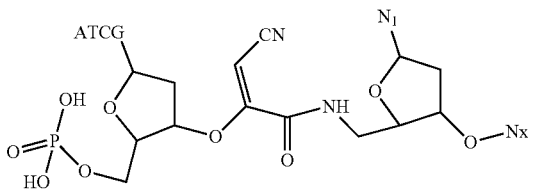

Formula XIV

The method for ligation between the chemical group and the sequencing base in Formula XIV may refer to the prior art, for example, PNAS, 2006. 103, 19635-19640.

Excision method: 100 Mm THPP, pH 9, 3M NaCl, 0.2M tris.

(5) Inosine Site Ligation Mode

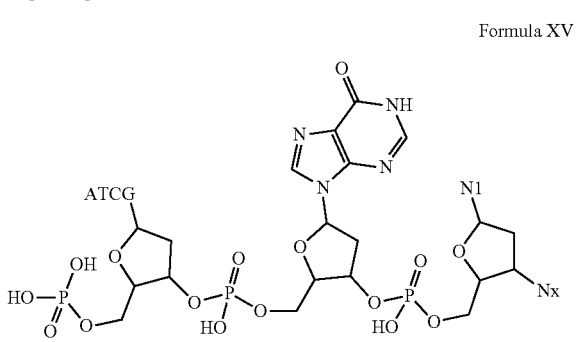

Formula XV

Inosine:

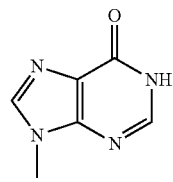

The method for ligation between the chemical group and the sequencing base in Formula XV may refer to the prior art, or the ligation may be carried out by a commissioned commercial company (e.g., Biotech Biotechnology (Shanghai) Co., Ltd.).

Excision method: 50 mM KOOCCH$_3$, 20 mM Tris-Acetate, 10 mM Mg(OOCCH$_3$)$_2$, 1 mM DTT, 100 µg/mL BSA, 2 U/mL hAAG enzyme+40 U/ml endonuclease IV enzyme.

Another aspect of the invention relates to a nucleic acid probe combination, which comprises 4 groups of probes, wherein:

the first group of nucleic acid probes (referred to as A probes): comprising the nucleic acid probe according to any one of items of the present invention, wherein the base of the first moiety is A;

the second group of nucleic acid probes (referred to as T probes): comprising the nucleic acid probe according to any one of items of the present invention, wherein the base of the first moiety is T or U;

the third group of nucleic acid probes (referred to as C probes): comprising the nucleic acid probes according to any one of items of the present invention, wherein the base of the first moiety is C;

the fourth group of nucleic acid probes (referred to as G probes): comprising the nucleic acid probes according to any one of items of the present invention, wherein the base of the first moiety is G;

and the detectable labels in the 4 groups of nucleic acid probes are different from each other;

the 4 groups of nucleic acid probes are mixed or not mixed;

preferably, the mole numbers of the first group of nucleic acid probes and the fourth group of nucleic acid probes are equal;

preferably, the mole numbers of the second group of nucleic acid probes and the third group of nucleic acid probes are equal;

preferably, the sum of the mole numbers of the first group of nucleic acid probes and the fourth group of nucleic acid probes is less than or equal to the sum of the mole numbers of the second group of nucleic acid probes and the third group of nucleic acid probes.

Without being bound by any theory, the A probe and the G probe are easier to ligated; preferably, the sum of the mole numbers of the A probes and the G probes is less than or equal to the sum of the mole numbers of the T probes and the C probes, which is conducive to the balance and efficiency of the ligation.

Preferably, the molar ratio of A probes:T probes:C probes:G probes is (0.5-2):(2-5):(2-5):(0.5-2);

preferably, the molar ratio of A probes:T probes:C probes:G probes is (0.8-1.5):(2-5):(2-5):(0.8-1.5);

preferably, the molar ratio of A probes:T probes:C probes:G probes is (0.8-1.5):(3-5):(3-5):(0.8-1.5);

preferably, the molar ratio of A probes:T probes:C probes:G probes is (0.5-2):(3-5):(3-5):(0.5-2); more preferably 1:4:4:1.

Without being bound by any theory, the preferred molar ratios of A probes:T probes:C probes:G probes are conducive to the balance and efficiency of the ligation.

Another aspect of the present invention relates to a ligation solution, which comprises the nucleic acid probe according to any one of items of the present invention or the nucleic acid probe combination of the present invention, and a DNA ligase.

In one embodiment of the present invention, in the ligation solution, the DNA ligase is one or more selected from the group consisting of T4 DNA ligase, T7 DNA ligase, and T3 DNA ligase.

In one embodiment of the present invention, in the ligation solution, the concentration of the nucleic acid probe is 0.1 µM to 5 µM, preferably 1 µM.

In one embodiment of the present invention, in the ligation solution, the concentration of the DNA ligase is 0.01 µM to 2 µM or 0.1 µg/ml to 20 µg/ml, preferably 0.5 µM.

In one embodiment of the present invention, the ligation liquid further comprises the following components:

50 mM $CH_3COOK$, 20 mM Tris, 10 mM $Mg(CH_3COO)_2$, 100 µg/ml BSA, 1 mM ATP, 10% PEG6000;

preferably, the remaining amount of the ligation liquid is water.

A further aspect of the present invention relates to a kit, which comprises the nucleic acid probe according to any one of items of the present invention, or the nucleic acid probe combination of the present invention, or the ligation solution of the present invention;

preferably, which further comprises one or more selected from the group consisting of a reagent capable of cleaving the ligation between the first moiety and the linker, a buffer for dissolving the nucleic acid probe, and a sequencing primer;

preferably, the reagents in the kit are free of silver ion.

In one embodiment of the present invention, in the kit, the DNA ligase is one or more selected from the group consisting of T4 DNA ligase, T7 DNA ligase, and T3 DNA ligase.

In one embodiment of the present invention, in the kit, the reagent capable of cleaving the ligation between the first moiety and the second moiety is an endonuclease (e.g., endonuclease IV or endonuclease V), an organic phosphide (e.g., THPP or TCEP), or a complex of $PdCl_2$ and sulfonated triphenylphosphine.

Another aspect of the present invention relates to a method for sequencing a nucleic acid, comprising the following steps:

(1) hybridizing a sequencing primer to a nucleic acid molecule to be tested;

(2) ligating the nucleic acid probe according to the present invention or the nucleic acid probe combination of the present invention to the sequencing primer;

(3) eluting the nucleic acid probe that has not bound to the nucleic acid molecule to be tested;

(4) detecting the detectable label of the nucleic acid probe binding to the nucleic acid molecule to be tested, and determining the base information of the first moiety;

(5) cleaving the ligation between the first moiety of the nucleic acid probe and the linker, and eluting the rest of the nucleic acid probe except the first moiety;

preferably, further comprising the following steps:

(6) repeating the above steps (2) to (4) or (2) to (5).

In one embodiment of the present invention, the nucleic acid molecule to be tested in the step (1) is ligated to a solid support.

The solid support includes, but is not limited to, a chip, a flow cell, a magnetic bead, and the like. A linker sequence is fixed on the solid support, and the linker sequence is capable of binding to the nucleic acid molecule to be tested. For example, when the nucleic acid molecule to be tested is in the form of a DNA library, the linker sequence is ligated to the linker sequence for constructing the library through base pairing. The method for constructing the DNA library may be a method known to those skilled in the art.

Preferably, the method for sequencing a nucleic acid further comprises a step of amplifying the nucleic acid molecule to be tested that is ligated to the solid support.

Without being bound by any theory, the purpose of amplification is to obtain a sufficient number of samples and amplify the signal intensity of the bases so to achieve the signal requirements for the sequencing. The amplification products are also ligated to the solid phase, thereby forming a local enrichment.

The method for the amplification may be a polymerase chain reaction (PCR), for example, Emulsion PCR or bridge PCR. The emulsion PCR may refer to, for example, the emulsion PCR operation in the SOLiD sequencing method of ABI company, or refer to the emulsion PCR operation in the Roche 454 sequencing method. The bridge PCR may refer to the bridge PCR operation in the Solexa sequencing method of Illumina Company.

In one embodiment of the present invention, in the step (2), the nucleic acid probe according to the present invention or the nucleic acid probe combination of the present invention is ligated to a sequencing primer by using the ligation solution of the present invention. The ligation of the probe in the step (1) is the same as that of other sequencing-by-ligation methods, which is a universal T4 DNA ligase ligation reaction.

In one embodiment of the present invention, in the step (3), the reagent used for the elution may be a reagent known to those skilled in the art, for example, 5×SSC+0.05% Tween20.

In one embodiment of the present invention, in the step (5), the reagent used for elution may be a reagent known to those skilled in the art, for example, 5×SSC+0.05% Tween20.

In an embodiment of the present invention, in the step (5), after the ligation between the first moiety of the nucleic acid probe and the linker is cleaved, the 3'-terminal OH is exposed, and the next cycle of sequencing-by-ligation can be performed (as shown in FIG. 1).

As for the step (6), in general, the above steps (1) to (5) are repeated; if a round of sequencing has been completed, only the above steps (1) to (4) may be repeated.

In the present invention, the nucleic acid molecule to be tested may be a single-stranded or double-stranded DNA molecule, or a single-stranded or double-stranded RNA molecule. The DNA molecule may be a DNA molecule from an animal, a plant, or a microorganism. Preferably, the DNA molecule is in the form of a DNA library, and the DNA library may be a DNA library constructed using a library construction kit.

In the present invention, Nx means that there are x N bases, and x may be a positive integer, such as 3, 4, 5, 6, 7, 8, 9, . . . 14, 15, and the like.

The term "random base" means that each of the 4 bases occupies 25% of the position.

The term "universal base" means that the base can form a base-pairing structure with any one of the 4 kinds of AGTC, such as 5-nitroindole ring, 2-nitropyrrole ring, and the like.

The term "sequencing base" means that the base at the position is a fixed base, for example, if the base at the position is T, the probe is responsible for detecting base A.

In the present invention, the term "$C_1$-$C_6$ alkyl" refers to a straight or branched alkyl having 1 to 6 carbon atoms, such as methyl, ethyl, propyl, isopropyl, n-butyl, sec-Butyl, tert-butyl, pentyl, 2-pentyl, isopentyl, neopentyl, hexyl, 2-hexyl, 3-hexyl, etc.; $C_1$-$C_4$ alkyl and $C_1$-$C_3$ alkyl can be understood similarly. The preferred alkyl group is a $C_1$-$C_4$ alkyl, and the more preferred alkyl group is a $C_1$-$C_3$ alkyl.

The term "$C_2$-$C_6$ alkenyl" refers to an alkenyl having 2 to 6 carbon atoms and at least one double bond, and includes vinyl, propenyl, 1-but-3-enyl, 1-pent-3-enyl, 1-hex-5-enyl, etc.; $C_3$-$C_5$ alkenyl can be similarly understood. $C_3$-$C_5$ alkenyl is preferred.

The term "$C_2$-$C_6$ alkynyl" refers to a hydrocarbon group having 2 to 6 carbon atoms and at least one triple bond, and includes ethynyl, propynyl, butynyl, pentyn-2-yl, etc.; $C_3$-$C_5$ alkynyl can be understood similarly. $C_3$-$C_5$ alkynyl is preferred.

The Beneficial Effects of the Present Invention

The invention has one or more of the following technical effects:
(1) The probes or the probe combinations or the sequencing methods of the present invention can significantly reduce the number or kinds of probes in the sequencing, thereby significantly reducing costs.
(2) Since only one base is added at a time, it is not required to repeatedly add primers, and thus the cost is also reduced.
(3) The present invention also uses an excision method that is friendly to the sequencing reaction system.
(4) The present invention has high sequencing accuracy.
(5) The present invention is beneficial to improve the reads of the sequencing.

BRIEF DESCRIPTION OF THE DRAWINGS

FIG. 1 shows a schematic diagram of excising AP site-containing probes under the action of endonuclease IV.

SPECIFIC MODELS FOR CARRYING OUT THE INVENTION

The embodiments of the present invention will be described in detail below with reference to examples, but those skilled in the art will understand that the following examples are only used to illustrate the present invention and should not be considered as limiting the scope of the present invention. If the specific conditions are not indicated in the examples, the conventional conditions or the conditions recommended by the manufacturer are used. If the reagents or instruments used are not specified by the manufacturer, they are all conventional products that are commercially available.

The nucleic acid probes used in the following examples can be synthesized according to the methods known in the art, and unless otherwise specified, they were synthesized by a commissioned commercial company, such as Heya Medical Technology (Shanghai) Co., Ltd. or Biotech Biotechnology (Shanghai) Co., Ltd.

Example 1: Sequencing Application of AP Site Reversible Ligation Probe (6 Random Bases)

1. Instruments and Reagents

The instrument was based on a BGISEQ-500 platform. Theoretically, other sequencing platforms (such as Illumina's Hiseq platform, etc.) could be appropriately adjusted to perform the experiments the same as or similar to those in this example.

In addition, in order to enable the application on the BGISEQ-500 platform, the selected modified dye had absorption and emission wavelengths similar to those of the dye used by the BGISEQ-500 reagent, so that it could be well detected by the BGISEQ-500 optical system.

Some of the reagents used in this experiment were completely the same as those of BGISEQ-500, including the photographic buffer reagent and elution buffer 2 used in this experiment.

Some reagents used in this experiment were different from those of BGISEQ-500, including: a ligation solution containing "the probes, enzymes and buffers of this example" was used to replace the probe polymerization reaction solution in BGISEQ-500, and the excision buffer of this experiment was used to replace the excision buffer of BGISEQ-500.

The experimental sample was the genomic DNA of *E. coli*, which was a standard sample carried by BGISEQ-500.

According to the manufacturer's instructions, MGIEasy™ DNA library preparation kit (Shenzhen Huada Zhizao Technology Co., Ltd.) was used to extract DNA from *E. coli* standard strains as raw materials for preparing a library for sequencing, and the library was loaded on a sequencing chip.

2. Design and Synthesis of Probes

Four groups of AP site reversible ligation probes were as follows (x=6):

The first group (A probes): the first moiety, i.e., the sequencing base was A, and the second moiety was 6 random bases.

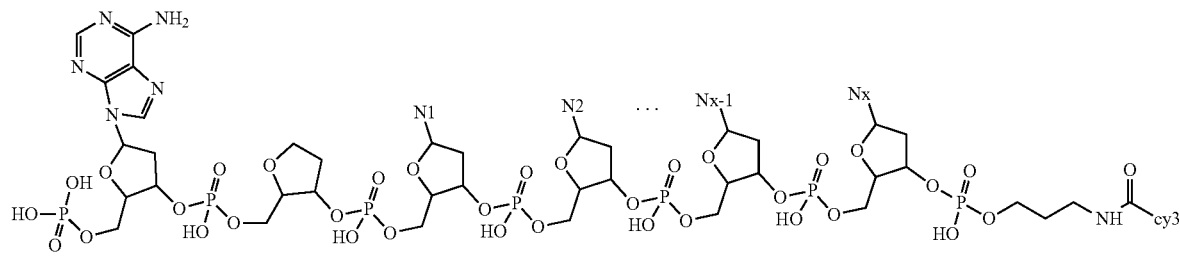

The second group (T probes): the first moiety, i.e., the sequencing base was T, and the second moiety was 6 random bases.

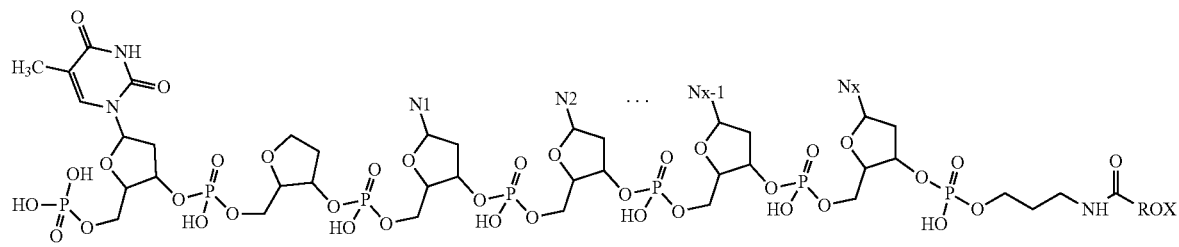

The third group (C probes): the first moiety, i.e., the sequenced base was C, and the second moiety was 6 random bases.

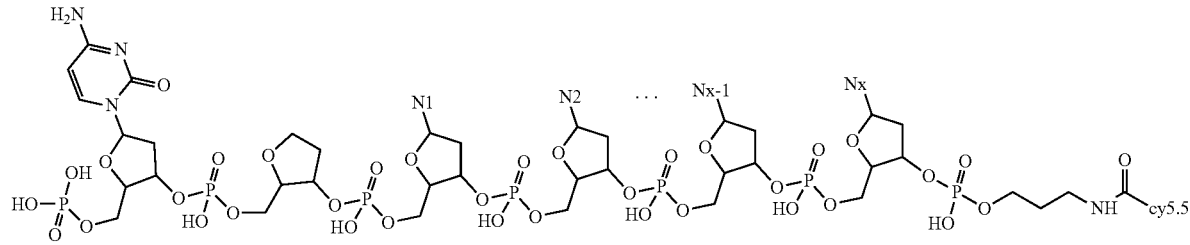

The fourth group (G probes): the first moiety, i.e., the sequencing base was G, and the second moiety was 6 random bases.

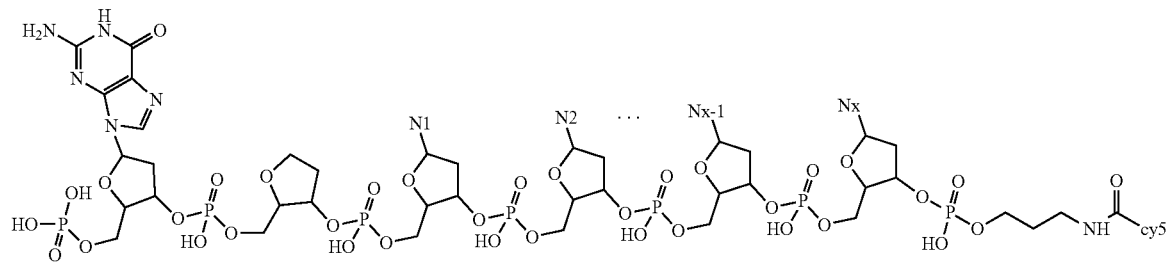

Biosynthetic Engineering (Shanghai) Co., Ltd. was commissioned to synthesize the above probes.

The above 4 groups of probes and T4 DNA ligase were dissolved in the following buffer:

50 mM $CH_3COOK$, 20 mM Tris, 10 mM $Mg(CH_3COO)_2$, 100 μg/ml BSA, 1 mM ATP, 10% PEG6000.

A ligation solution was obtained.

In the ligation solution, the concentration of the probes was 1 μM, in which the molar ratio of A probes:T probes:C probes:G probes was approximately 1:4:4:1.

In the ligation solution, the concentration of the DNA ligase was 0.5 μM.

3. Sequencing Steps

Referring to the instruction manual of BGISEQ-500, the following preliminary preparations were performed: library construction, a DNA single-stranded loop was amplified into DNA nanospheres, the DNA nanospheres were loaded on the chip carried by BGISEQ-500, and the sequencing primer was loaded on the DNA nanospheres.

A ligation solution containing the above four kinds of probes, a T4 DNA ligase and a buffer was added by using an instrument, and the ligation reaction was performed at 25° C. for 30 minutes;

The elution reagent 2 was used to elute the probes that were not ligated;

Then a photographic buffer was added for image acquisition (photographing); and a software was used to analyze the base information of each DNA nanosphere site;

After taking the picture, endonuclease IV (New England Biolabs, article number M0304L) and buffer thereof were added, and the reaction was performed at 37° C. for 5 minutes to excise the AP site, and then the elution reagent 2 was added to elute the excised moiety of the probe;

The 4 groups of probes could be added repeatedly to perform the next cycle of sequencing.

4. Experimental Results

The result was completely consistent with the sequence of the standard sample carried by BGISEQ-500, indicating that the sequencing method of the present invention was accurate.

Example 2: Sequencing Application of AP Site Reversible Ligation Probe (3 Random Bases+3 Universal Bases)

This example was performed by substantially the same method as that in Example 1, except that the following 4 groups of probes were used:

The first group (A probes): the first moiety, i.e., the sequencing base was A, and the second moiety was 3 random bases+3 universal bases.

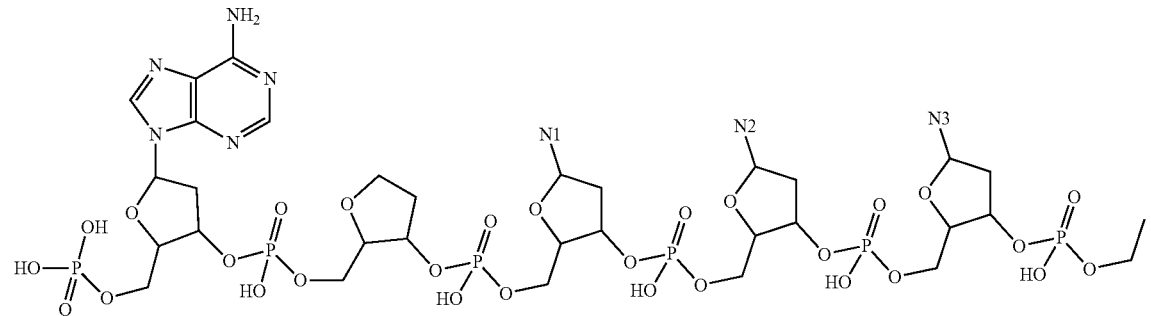

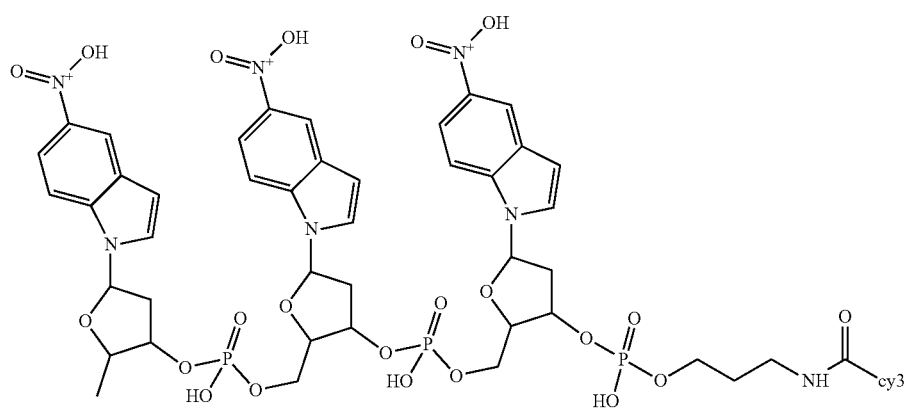

The second group (T probes): the first moiety, i.e., the sequencing base was T, and the second moiety was 3 random bases+3 universal bases.
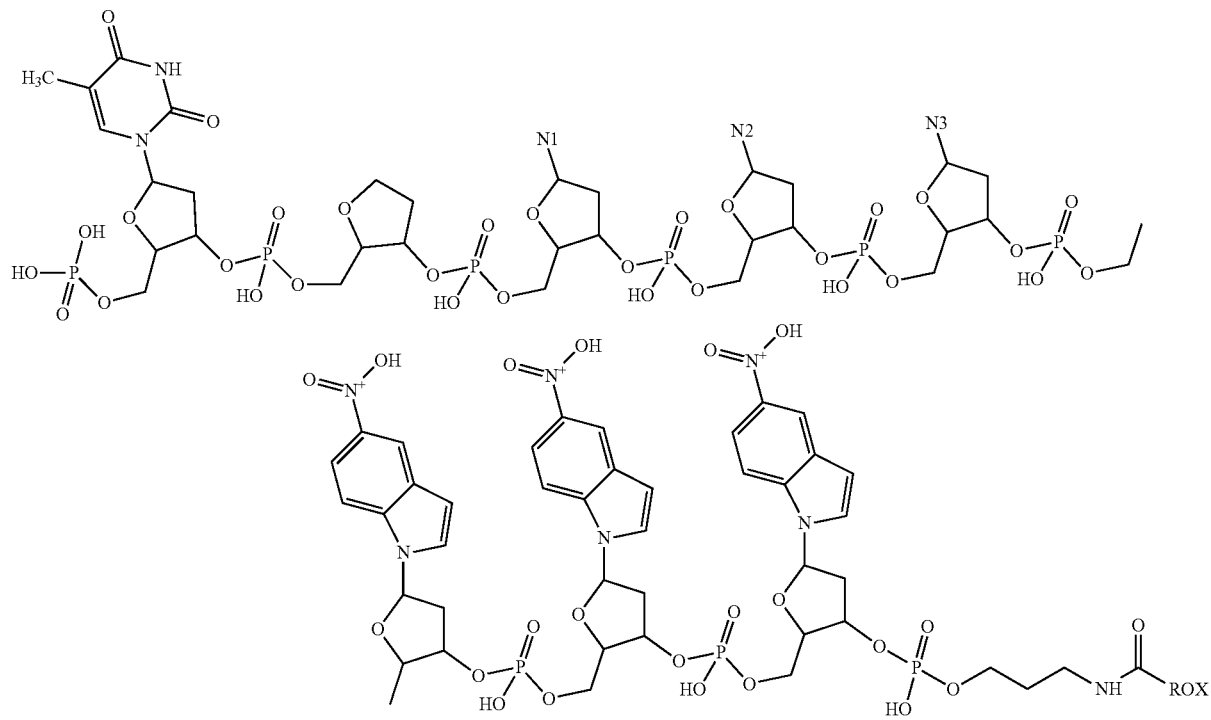
The third group (C probes): the first moiety, i.e., the sequenced base was C, and the second moiety was 3 random bases+3 universal bases.
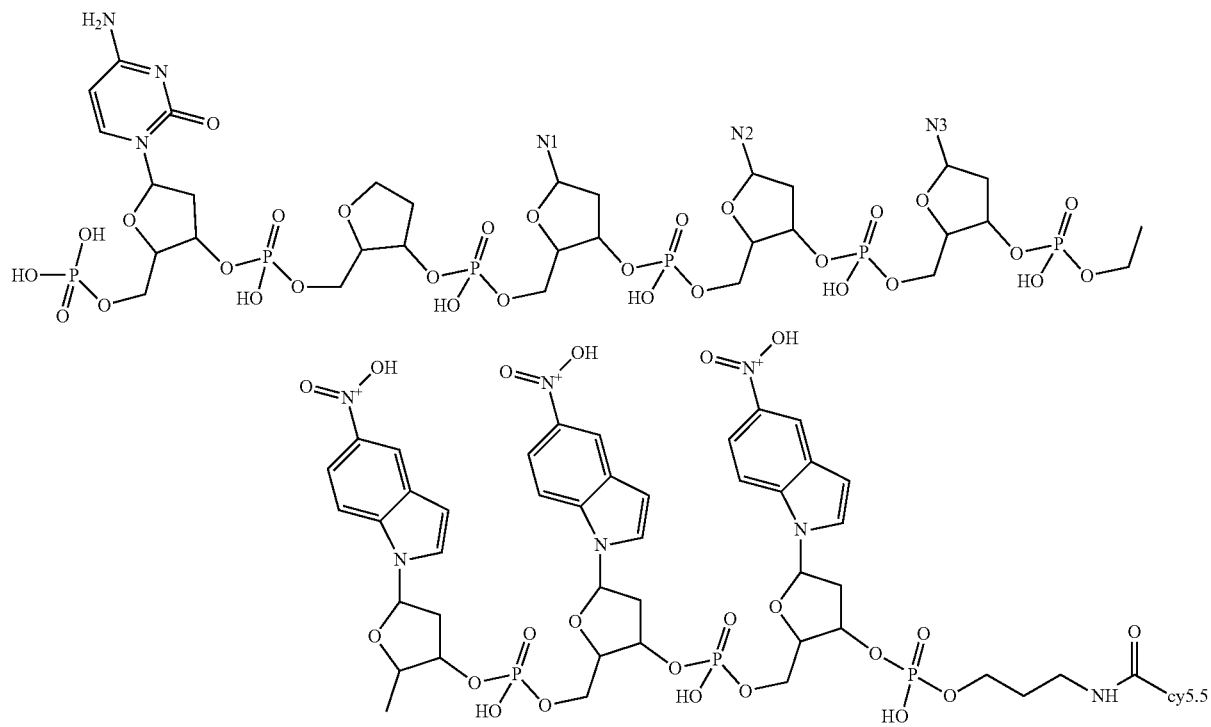

The fourth group (G probes): the first moiety, i.e., the sequencing base was G, and the second moiety was 3 random bases+3 universal bases.

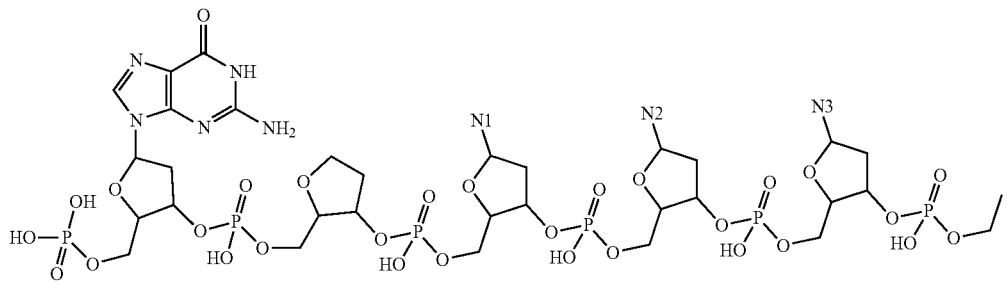

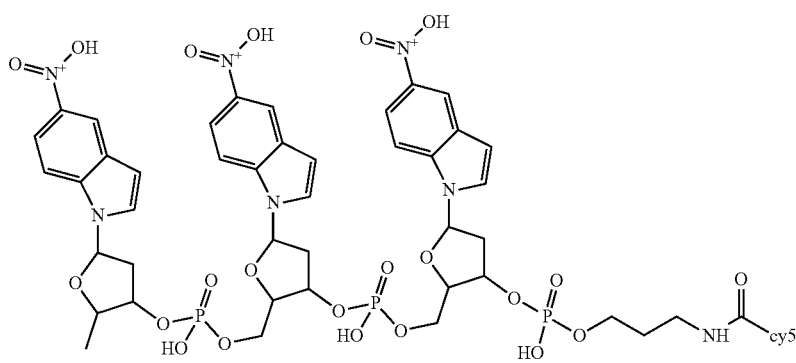

The result was completely consistent with the sequence of the standard sample carried by BGISEQ-500, indicating that the sequencing method of the present invention was accurate.

Example 3: Sequencing Application of AP Site Reversible Ligation Probe (7 Random Bases)

This example was performed by substantially the same method as that in Example 1, except that the 4 groups of AP site reversible ligation probes were used, where x=7.

The result was completely consistent with the sequence of the standard sample carried by BGISEQ-500, indicating that the sequencing method of the present invention was accurate.

Example 4: Sequencing Application of AP Site Reversible Ligation Probe (8 Random Bases)

This example was performed by substantially the same method as that in Example 1, except that the 4 groups of AP site reversible ligation probes were used, where x=8.

The result was completely consistent with the sequence of the standard sample carried by BGISEQ-500, indicating that the sequencing method of the present invention was accurate.

Example 5: Sequencing Application of AP Site Reversible Ligation Probe (9 Random Bases)

This example was performed by substantially the same method as that in Example 1, except that the 4 groups of AP site reversible ligation probes were used, where x=9.

The result was completely consistent with the sequence of the standard sample carried by BGISEQ-500, indicating that the sequencing method of the present invention was accurate.

Example 6: Sequencing Application of Chemical Group (Azide) Reversible Ligation Probe (6 Random Bases)

This example was performed by substantially the same method as that in Example 1, except the following differences:

1. Instruments and Reagents

The same as those in Example 1.

2. Design and Synthesis of Probes

The following 4 groups of probes were used, where x=6:

The first group (A probes): the first moiety, i.e., the sequencing base was A, and the second moiety was 6 random bases.

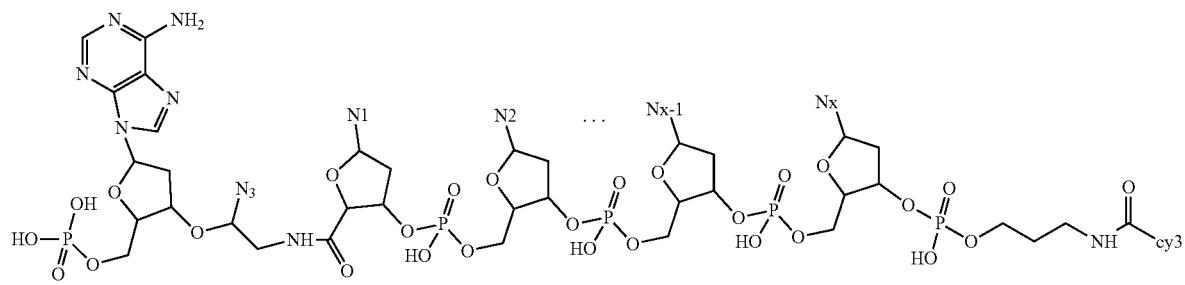
The second group (T probes): the first moiety, i.e., the sequencing base was T, and the second moiety was 6 random bases.
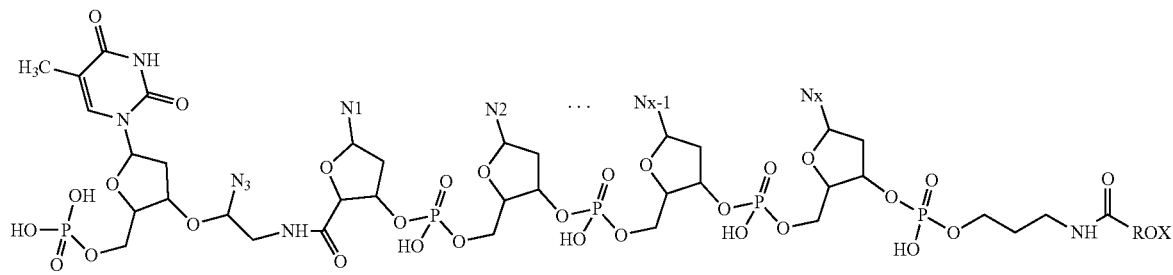
The third group (C probes): the first moiety, i.e., the sequenced base was C, and the second moiety was 6 random bases.
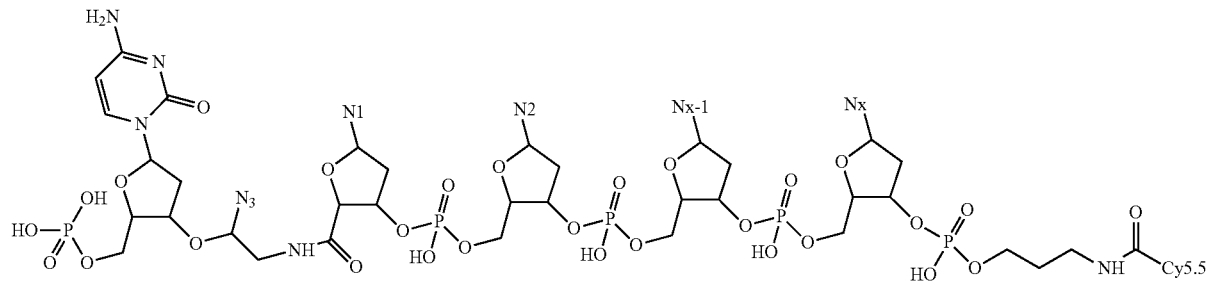
The fourth group (G probes): the first moiety, i.e., the sequencing base was G, and the second moiety was 6 random bases.
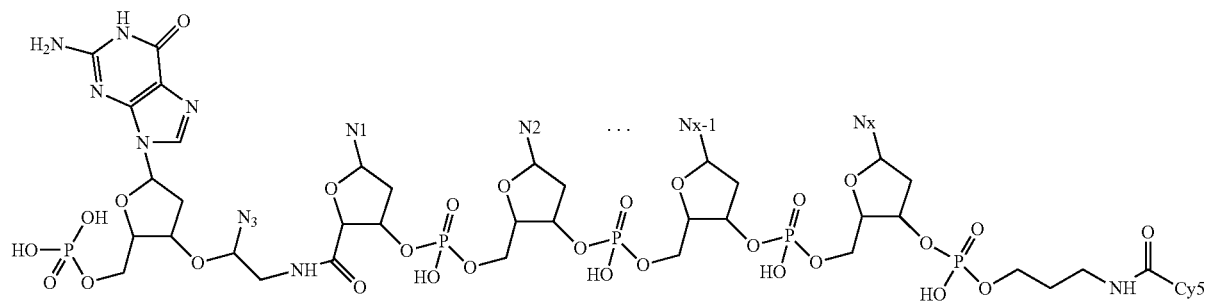

The above 4 groups of probes and T4 DNA ligase were dissolved in the following buffer:

50 mM $CH_3COOK$, 20 mM Tris, 10 mM $Mg(CH_3COO)_2$, 100 μg/ml BSA, 1 mM ATP, 10% PEG6000.

A ligation solution was obtained.

In the ligation solution, the concentration of the probes was 1 μM, in which the molar ratio of A probes:T probes:C probes:G probes was approximately 1:4:4:1.

The concentration of T4 DNA ligase in the ligation solution was 0.5 μM.

3. Sequencing Steps

Referring to the instruction manual of BGISEQ-500, the following preliminary preparations were completed: library construction, a DNA single-stranded loop was amplified into DNA nanospheres, the DNA nanospheres were loaded on the chip carried by BGISEQ-500, and sequencing primers was loaded on the DNA nanospheres.

A ligation solution containing the above 4 kinds of probes, a T4 DNA ligase and a buffer was added by using an instrument, and the ligation reaction was performed at 25° C. for 30 minutes;

The elution reagent 2 was used to elute the probes that were not ligated;

Then a photographic buffer was added for image acquisition (photographing); and a software was used to analyze the base information of each DNA nanosphere site;

After taking the picture, an excision reagent (whose composition was: 10 Mm THPP, 200 Mm tris, pH=9 buffer, 0.5M sodium chloride) was used to perform the excision reaction at 60° C. for 3 minutes, and then the elution reagent 2 was added to elute the excised moiety of the probe;

The 4 groups of probes could be added repeatedly to perform the next cycle of sequencing.

4. Experimental Results

Due to the small genome of *E. coli*, the inventors herein performed 30 cycles of sequencing, and the results were analyzed with the sequencing analysis software of BGISEQ-500. The results were shown in Table 1 below.

TABLE 1

| | |
|---|---|
| Reference Genome (Reference) | *E. coli* |
| Number of cycles (CycleNumber) | 30 |
| Photographing area (number of areas) | 1632 |
| Total reads (TotalReads) | 352.89M |
| Mapped reads (MappedReads) | 293.01M |
| [a] Q30 | 77.5% |
| Lagging phase (Lag) | 0.78% |
| Leading phase (Runon) | 0.39% |
| Effective reads ratio (ESR) | 80.73% |
| Mapping rate (MappingRate) | 83.3% |
| [b] Error rate | 1.83% |

[a] Q30 indicates the probability that a base is mismeasured is 0.1%, that was, the accuracy is 99.9%; Q30 is 77.5%, which means that the accuracy of the base call (77.5%) reaches 99.9%.
[b] it is an average error rate.

The results showed that the method of the present invention had a Q30 of 77.5%, the error rate was only 1.83%, and the reads could reach at least 30 bases. In addition, the cost of the present invention was significantly lower than that of the existing sequencing-by-ligation methods because that the number of probes was reduced and the replacement with new primers was not necessary.

Example 7: Sequencing Application of Chemical Group (Allyl) Reversible Ligation Probe (6 Random Bases)

This example was performed by substantially the same method as that in Example 1, except that the following 4 groups of chemical groups group (allyl) reversible ligation probes were used:

The first group (A probes): the first moiety, i.e., the sequencing base was A, and the second moiety was 6 random bases.

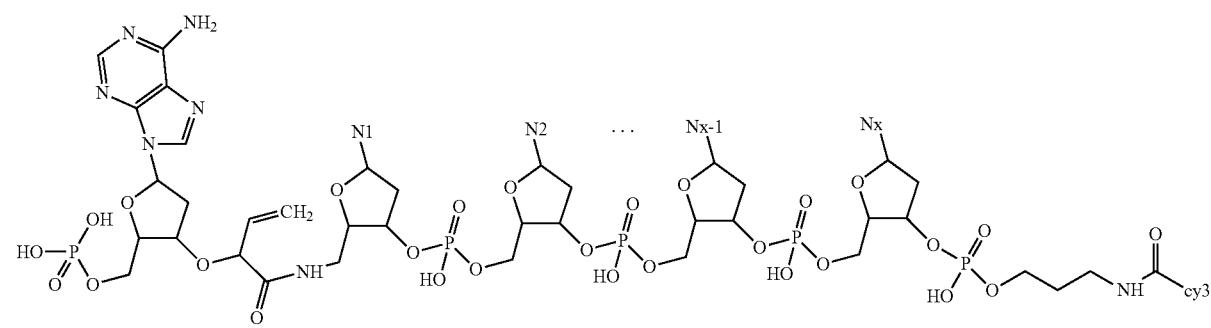

The second group (T probes): the first moiety, i.e., the sequencing base was T, and the second moiety was 6 random bases.
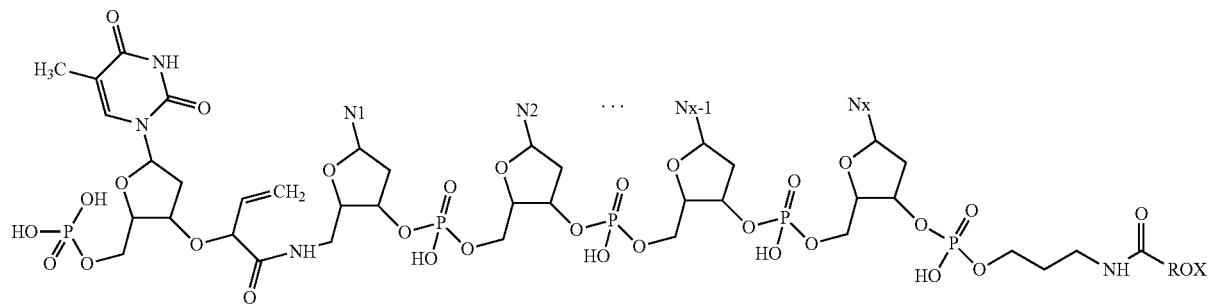
The third group (C probes): the first moiety, i.e., the sequenced base was C, and the second moiety was 6 random bases.
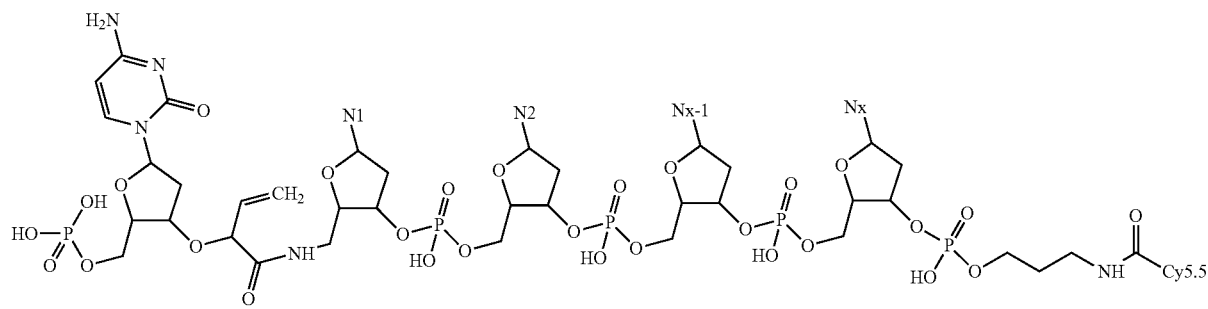
The fourth group (G probes): the first moiety, i.e., the sequencing base was G, and the second moiety was 6 random bases.
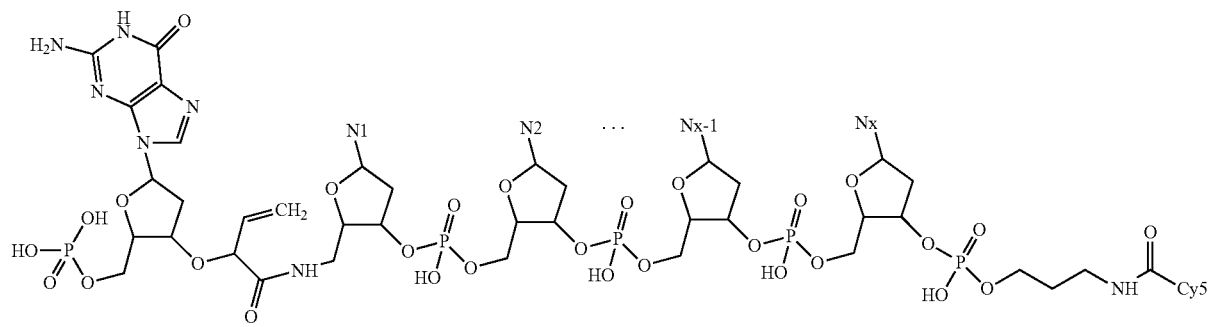

The result was completely consistent with the sequence of the standard sample carried by BGISEQ500, indicating that the sequencing method of the present invention was accurate.

Example 8: Sequencing Application of Chemical Group (Cyanovinyl) Reversible Ligation Probe (6 Random Bases)

This example was performed by substantially the same method as that in Example 1, except that the following 4 groups of chemical groups group (cyanovinyl) reversible ligation probes were used:

The first group (A probes): the first moiety, i.e., the sequencing base was A, and the second moiety was 6 random bases.

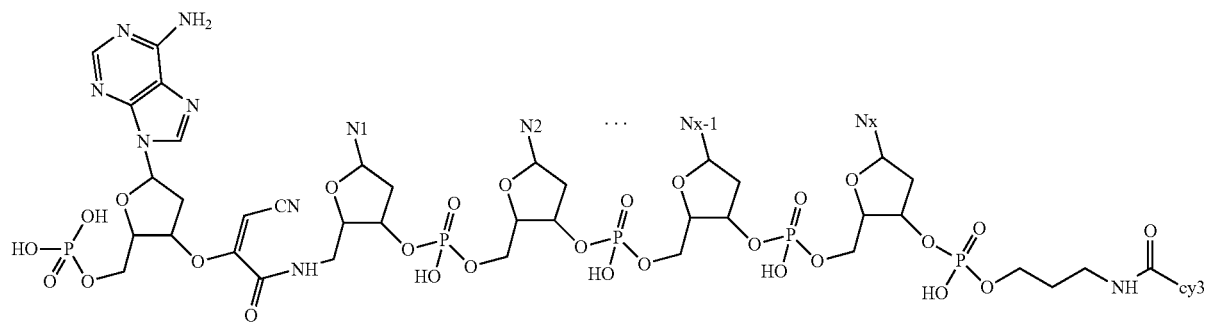

The second group (T probes): the first moiety, i.e., the sequencing base was T, and the second moiety was 6 random bases.

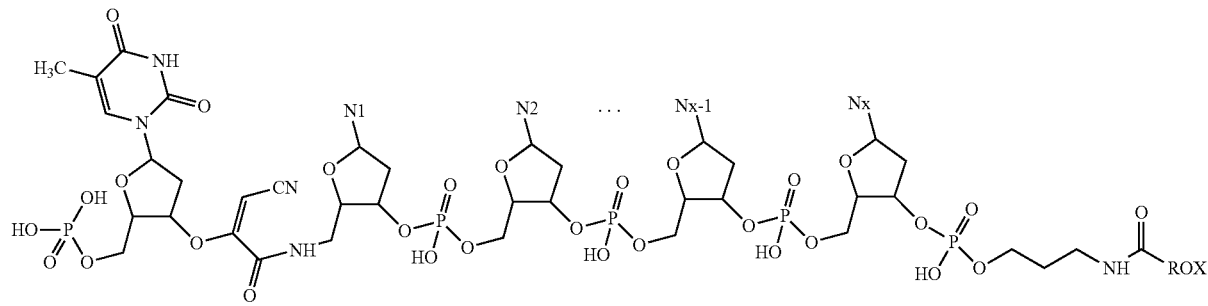

The third group (C probes): the first moiety, i.e., the sequenced base was C, and the second moiety was 6 random bases.

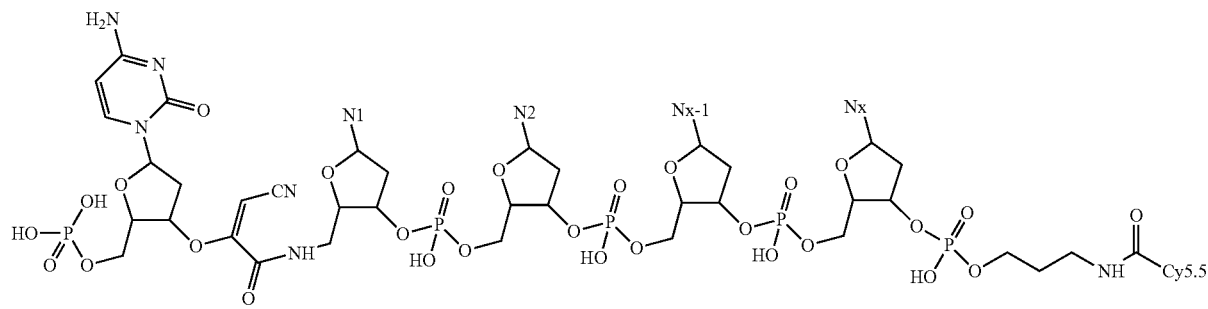

The fourth group (G probes): the first moiety, i.e., the sequencing base was G, and the second moiety was 6 random bases.

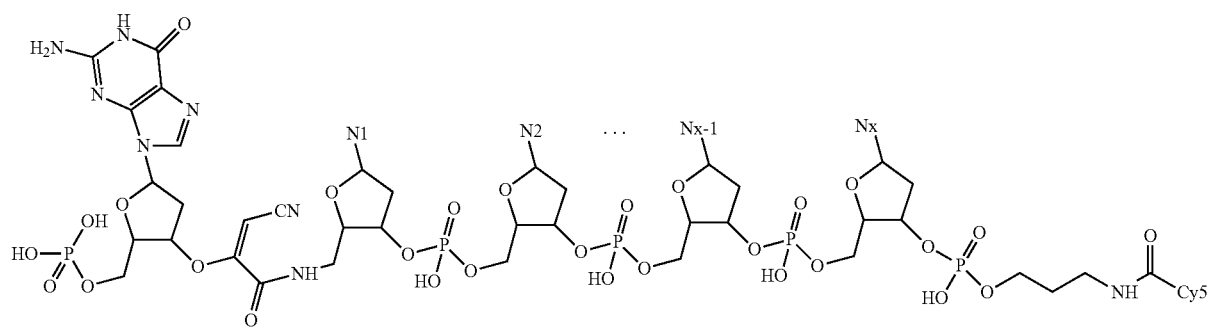

The result was completely consistent with the sequence of the standard sample carried by BGISEQ-500, indicating that the sequencing method of the present invention was accurate.

Example 9: Sequencing Application of Chemical Group (Inosine) Reversible Ligation Probe (6 Random Bases)

This example was performed by substantially the same method as that in Example 1, except that the following 4 groups of chemical groups group (Inosine) reversible ligation probes were used:

The first group (A probes): the first moiety, i.e., the sequencing base was A, and the second moiety was 6 random bases.

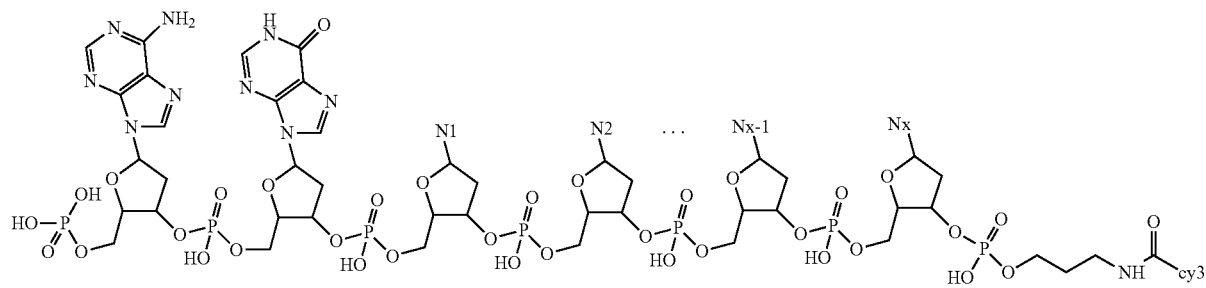

The second group (T probes): the first moiety, i.e., the sequencing base was T, and the second moiety was 6 random bases.

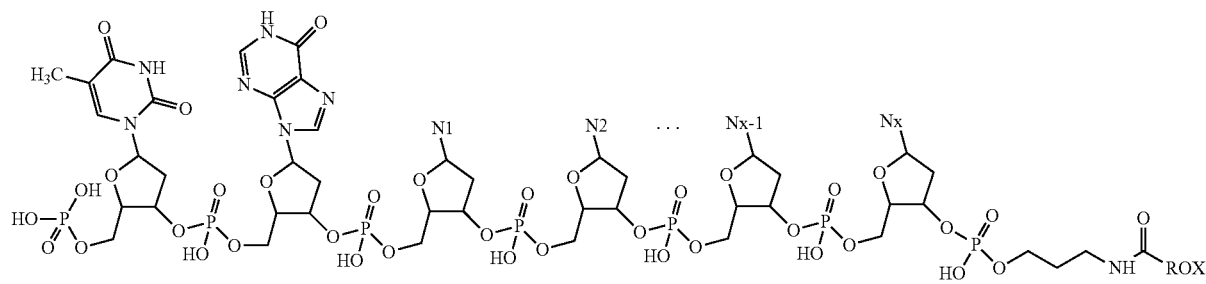

The third group (C probes): the first moiety, i.e., the sequenced base was C, and the second moiety was 6 random bases.

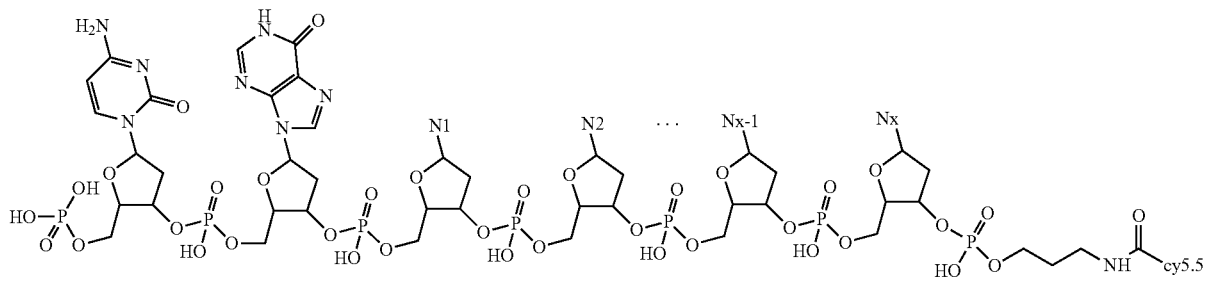

The fourth group (G probes): the first moiety, i.e., the sequencing base was G, and the second moiety was 6 random bases.

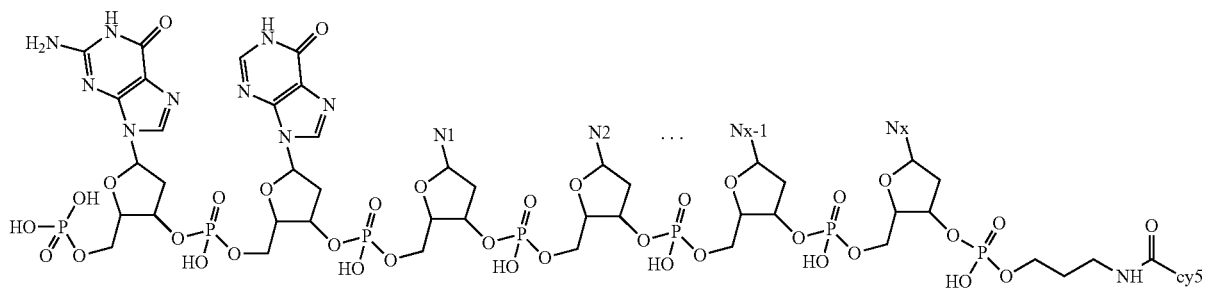

The result was completely consistent with the sequence of the standard sample carried by BGISEQ-500, indicating that the sequencing method of the present invention was accurate.

Although the specific embodiments of the present invention have been described in detail, those skilled in the art will understand that according to all the teachings that have been disclosed, various modifications and substitutions can be made to those details, and these changes are all within the protection scope of the present invention. The full scope of the invention is given by the appended claims and any equivalents thereof.

What is claimed is:

1. A nucleic acid probe combination, which comprises 4 groups of nucleic acid probes, wherein each group of nucleic acid probes contains a nucleic acid probe, wherein the nucleic acid probe comprises a first moiety, a second moiety, a linker and a detectable label, wherein:
   the first moiety has a base of A, T, U, C or G,
   the second moiety has random bases and/or universal bases, and the number of the bases is 3 or more,
   the first moiety is ligated to the second moiety via the linker, and the ligation between the first moiety and the linker can be cleaved,
   the detectable label is ligated to the second moiety or the linker; and
   the linker does not contain a sulfur atom;
   wherein:
   the first group of nucleic acid probes: comprising the nucleic acid probe of which the base of the first moiety is A;
   the second group of nucleic acid probes: comprising the nucleic acid probe of which the base of the first moiety is T or U;
   the third group of nucleic acid probes: comprising the nucleic acid probes of which the base of the first moiety is C;
   the fourth group of nucleic acid probes: comprising the nucleic acid probes of which the base of the first moiety is G;
   and the detectable labels in the 4 groups of nucleic acid probes are different from each other;
   the 4 groups of nucleic acid probes are mixed or not mixed;
   the mole number of the first group of nucleic acid probes and that of the fourth group of nucleic acid probes are equal;
   the mole number of the second group of nucleic acid probes and that of the third group of nucleic acid probes are equal;
   the sum of the mole number of the first group of nucleic acid probes and that of the fourth group of nucleic acid probes is less than or equal to the sum of the mole number of the second group of nucleic acid probes and that of the third group of nucleic acid probes; and
   the molar ratio of the first group of nucleic acid probes:the second group of nucleic acid probes:the third group of nucleic acid probes:the fourth group of nucleic acid probes is (0.5-2):(3-5):(3-5):(0.5-2); more preferably 1:4:4:1.

2. A kit, which comprises the nucleic acid probe combination according to claim 1;

preferably, the kit further comprises one or more selected from the group consisting of a reagent capable of cleaving the ligation between the first moiety and the linker, a buffer for dissolving the nucleic acid probe, and a sequencing primer;

preferably, the reagents in the kit are free of silver ion.

3. The kit according to claim 2, wherein the reagent capable of cleaving the ligation between the first moiety and the linker is an endonuclease, an organic phosphide, or a complex of $PdCl_2$ and sulfonated triphenylphosphine.

4. A ligation solution, which comprises the nucleic acid probe combination according to claim 1, and a DNA ligase.

5. The ligation solution according to claim 4, characterized in any one or more of the following (1) to (5):
   (1) the DNA ligase is one or more selected from the group consisting of T4 DNA ligase, T7 DNA ligase, and T3 DNA ligase;
   (2) the concentration of the nucleic acid probe is 0.1 µM to 5 µM, preferably 1 µM;
   (3) the concentration of the DNA ligase is 0.01 µM to 2 µM, preferably 0.5 µM;
   (4) further comprising the following components: 50 mM $CH_3COOK$, 20 mM Tris, 10 mM $Mg(CH_3COO)_2$, 100 µg/ml BSA, 1 mM ATP, 10% PEG6000;
   (5) the rest of the ligation liquid is water.

6. A method for sequencing nucleic acid, comprising the following steps:
   (1) hybridizing a sequencing primer to a nucleic acid molecule to be tested;
   (2) ligating the nucleic acid probe combination according to claim 1 to the sequencing primer;
   (3) eluting the nucleic acid probe that has not bound to the nucleic acid molecule to be tested;
   (4) detecting the detectable label of the nucleic acid probe binding to the nucleic acid molecule to be tested, and determining the base information of the first moiety;
   (5) cleaving the ligation between the first moiety of the nucleic acid probe and the linker, and eluting the rest of the nucleic acid probe except the first moiety;
   preferably, further comprising the following steps:
   (6) repeating the above steps (2) to (4) or (2) to (5).

7. The kit according to claim 3, wherein the endonuclease is endonuclease IV or endonuclease V.

8. The kit according to claim 3, wherein the organic phosphide is THPP or TCEP.

9. The nucleic acid probe combination according to claim 1, wherein the first moiety is located at the 5'-terminal or the 3'-terminal.

10. The nucleic acid probe combination according to claim 1, wherein the bases of the second moiety are 3 to 15 bases, preferably 5 to 12 bases, and more preferably 5 to 10 bases, particularly preferably 6 to 9 bases.

11. The nucleic acid probe combination according to claim 1, wherein the detectable label is a fluorophore; preferably one or more selected from the group consisting of cy3, cy5, Texas Red, 6-FAMTM, AF532, AF647 and AF688;
   preferably, the detectable label is ligated to the second moiety;
   preferably, the detectable label is ligated to 3'-OH at the end of the second moiety;
   preferably, the detectable label is ligated to 3'-OH at the end of the second moiety via a phosphoester bond.

12. The nucleic acid probe combination according to claim 1, wherein the linker is selected from the group represented by the following Formula IV to Formula IX:

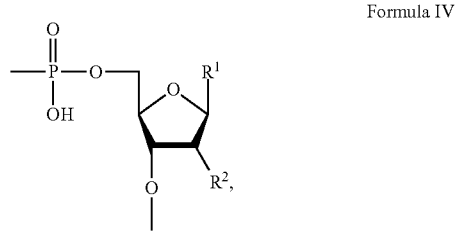
Formula IV

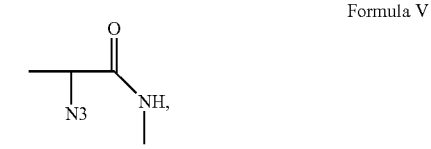
Formula V

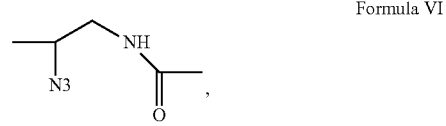
Formula VI

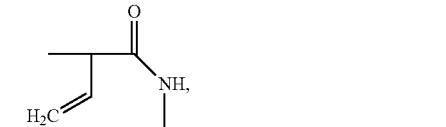
Formula VII

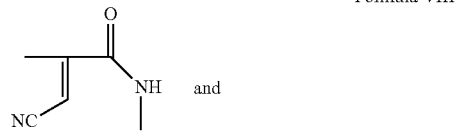
Formula VIII and

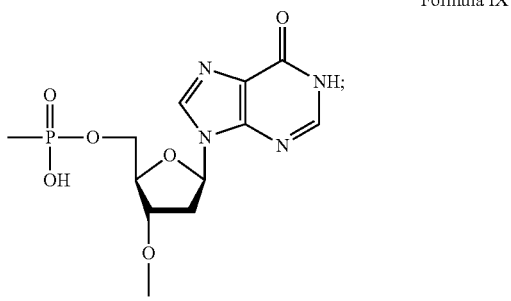
Formula IX wherein, in Formula IV, $R^1$ is selected from a group consisting of H, OH, $C_1$-$C_6$ alkyl, $C_2$-$C_6$ alkenyl, and $C_2$-$C_6$ alkynyl; $R^2$ is selected from a group consisting of H, OH, F, Cl, and Br.

13. The nucleic acid probe combination according to claim 1, wherein the molar ratio of the first group of nucleic acid probes:the second group of nucleic acid probes:the third group of nucleic acid probes:the fourth group of nucleic acid probes is 1:4:4:1.

* * * * *